US00PP24976P3

(12) United States Plant Patent van Straaten et al.

(10) Patent No.: US PP24,976 P3
(45) Date of Patent: Oct. 21, 2014

(54) **VARIETY OF *HYDRANGEA* PLANT NAMED 'STRAMINI'**

(50) Latin Name: *Hydrangea macrophylla*
Varietal Denomination: Stramini

(76) Inventors: Jan van Straaten, Harderwijk (NL); Johan van Straaten, Harderwijk (NL)

( * ) Notice: Subject to any disclaimer, the term of this patent is extended or adjusted under 35 U.S.C. 154(b) by 158 days.

(21) Appl. No.: 13/506,883

(22) Filed: May 22, 2012

(65) Prior Publication Data

US 2013/0318666 P1 Nov. 28, 2013

(51) Int. Cl.
*A01H 5/00* (2006.01)

(52) U.S. Cl.
USPC ..... Plt./250

(58) Field of Classification Search
USPC ..... Plt./250
See application file for complete search history.

(56) References Cited

PUBLICATIONS

HTML Color Names, retrieved on Dec. 20, 2013, retrieved from the Internet at <http://www.w3schools.com/html/html_colornames.asp> copyright 1999-2013, 5 pp.*
Pluto Upov Plant Variety Database 201303, retrieved on Dec. 5, 2013, retrieved from the Internet at <https://www3.wipo.int/pluto/user/en/index.jsp> one page.*

* cited by examiner

*Primary Examiner* — June Hwu
(74) *Attorney, Agent, or Firm* — The Webb Law Firm

(57) ABSTRACT

A new and distinct *Hydrangea* plant having multicolored flowers and strong stems.

2 Drawing Sheets

Botanical classification: *Hydrangea macrophylla.*
Varietal denomination: 'STRAMINI'.

BACKGROUND OF THE INVENTION

The present invention comprises a new and distinct cultivar of *Hydrangea* plant known by the varietal name 'Stramini'. The new variety was discovered in 2006 in a planned breeding program in Harderwijk, The Netherlands. The purpose of the breeding program was to develop *Hydrangeas* with improved green-like flower colors. The new variety is the result of a cross between breeding selection Seedling 1012 (female parent, unpatented) and Seedling HY 2586 (male parent, unpatented). The compact nature of 'Stramini' is similar to its female parent, but it differs from Seedling 1012 in flower color. The flower color of 'Stramini' is similar to its male parent, but it differs from Seedling HY 2586 in leaf shape. Further, 'Stramini' exhibits greener colored flowers than *Hydrangea* plant 'Elbtal' (upatented). The new variety was first asexually reproduced in 2007 via propagation by cuttings in Harderwijk, The Netherlands. The new variety has been trial and field tested in Harderwijk, The Netherlands and has been found to retain its distinctive characteristics and remain true to type through successive propagations.

The following traits distinguish 'Stramini' as a new and distinct cultivar from other *Hydrangea* varieties known to the breeder:

1. Multi colored flowers with a greenish hue; and
2. Strong stems.

DESCRIPTION OF THE DRAWINGS

The accompanying photographic drawings illustrate the new variety, with the color being as nearly true as is possible with color illustrations of this type.

DESCRIPTION OF THE PLANT

Figure 1:
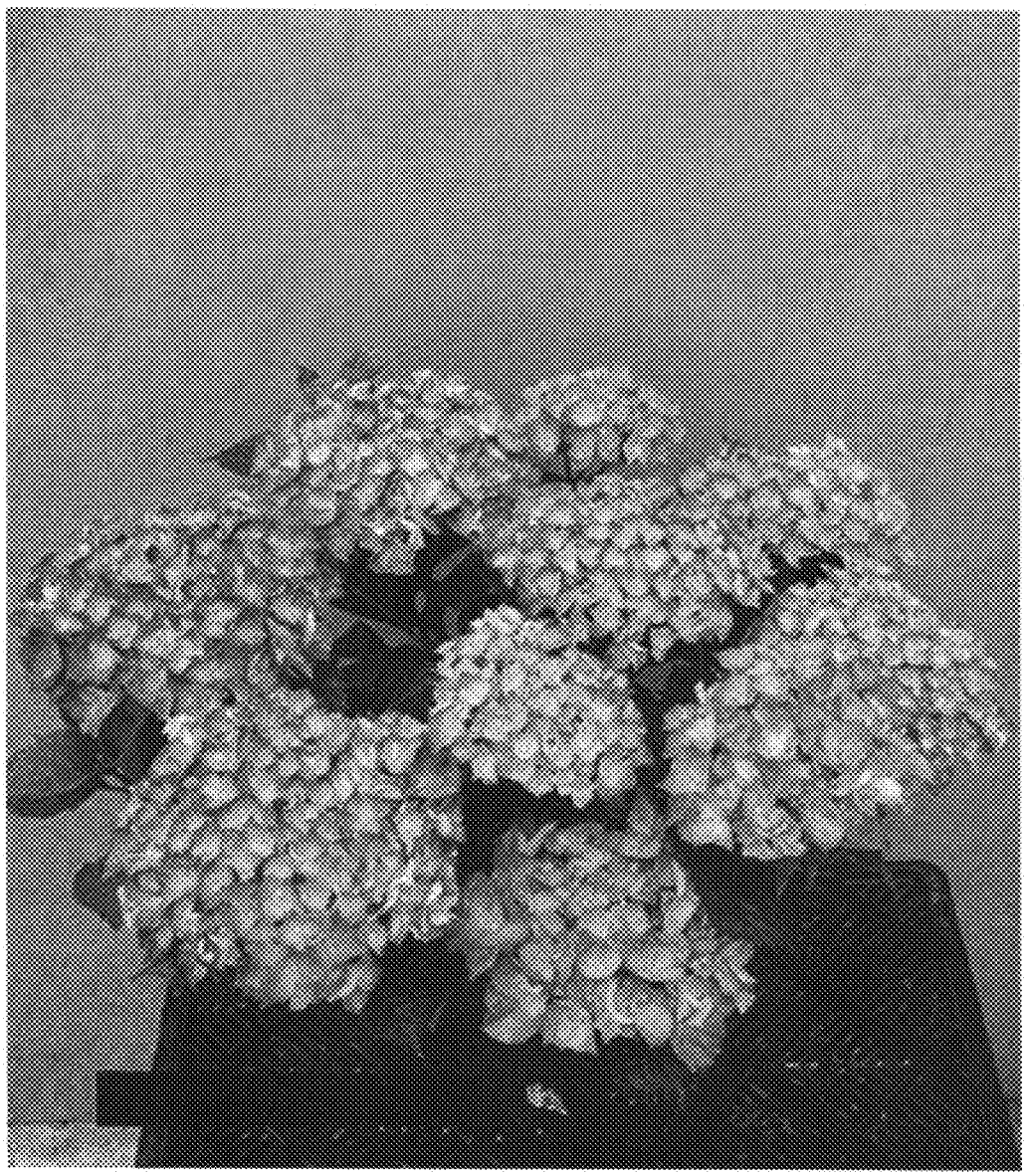
FIG. 1 is photograph of an entire plant of the new variety.
Figure 2:
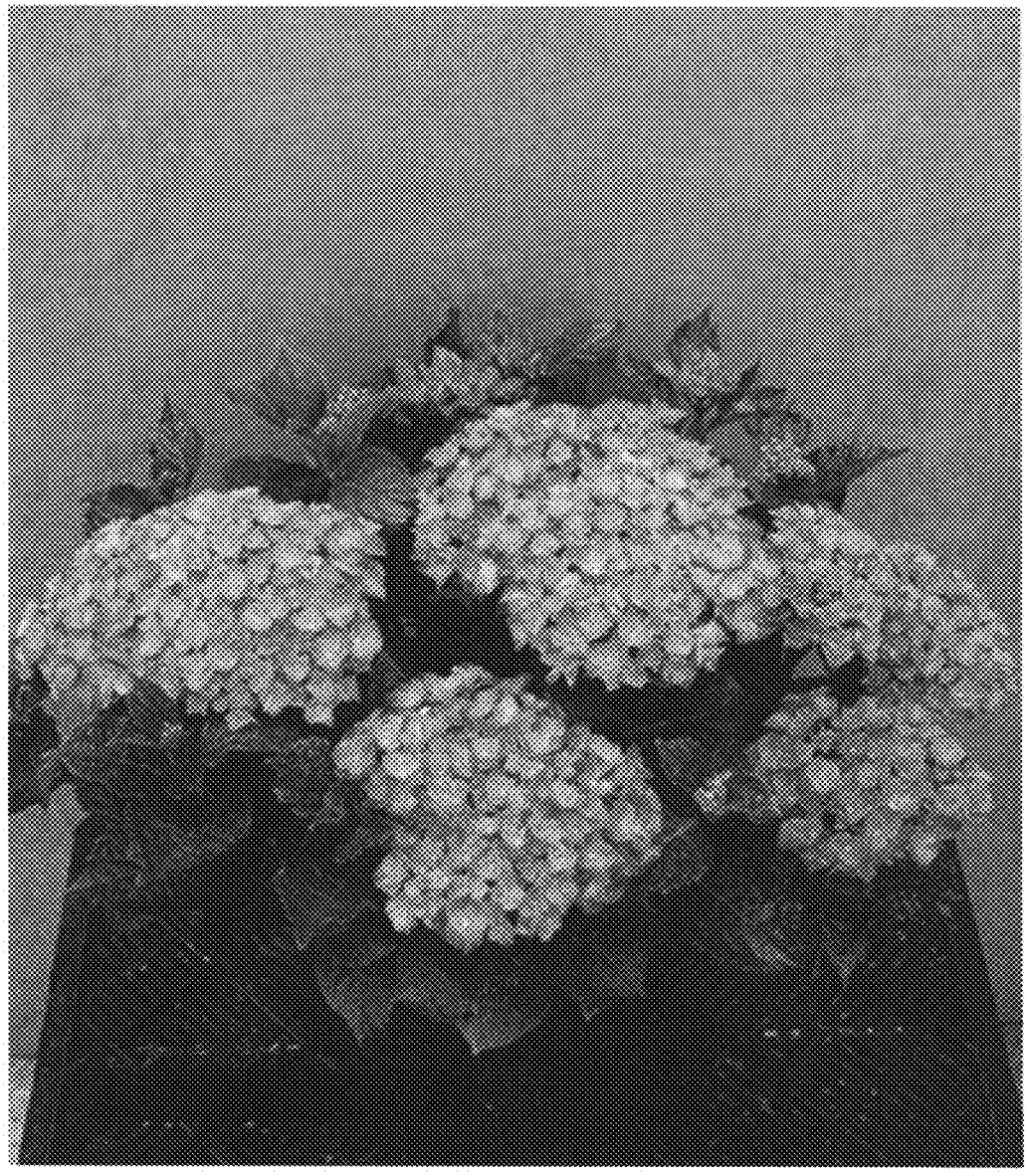
FIG. 2 is another photograph of the same plant of the new variety of FIG. 1, whereby color differences are due to differences in the flowering stage of the plant.

The following detailed description sets forth characteristics of the new cultivar. The plants were grown in 15 cm. pots, 8 per $m^2$, in ordinary potting soil with granulated fertilizers at a pH of 6.0. The plants were two years old when described. Measurements and color readings of the plants were taken in Harderwijk, The Netherlands under natural light. Color references are primarily to the HTML Color Chart.

PLANT

Time to initiate roots: About 14 days at 22° C.
Time to develop roots: About 18 days at 18-20° C.
Rooting habit: Moderate.
Time to produce a finished flowering plant from a rooted cutting: About 48 weeks in a 15 cm. container.
Form: Mounded.
Height (from media surface to top of foliage): 35-40 cm.
Height (from media surface to top of flowers): 40-45 cm.
Plant diameter: 35-40 cm.
Vigor: Good.
Strength: Good.
Branching habit: Moderately-branched.
Trunk:
*Main trunk length.*—8 cm.
*Diameter.*—1 cm.
*Color.*—6B 8E 23.
*Texture.*—Shiny.

*Pubescence*.—Absent.
*Internode length*.—1.5-2 cm.
Lateral branches:
*Length*.—Young: 5-10 cm. Mature: 25-30 cm.
*Diameter*.—Young: 0.5 cm. Mature: 0.5 cm.
*Internode length*.—6 cm.
*Texture*.—Shiny.
*Pubescence*.—Absent.
*Color*.—Young: Chartreuse 7F FF 00. Mature: Dark Green 00 64 00.
Foliage:
*Arrangement*.—Single.
*Stipules*.—None present.
*Size of leaf*.—Length: 12 cm. Width: 7-8 cm.
*Shape of leaf* (*generally*).—Young: Elliptic/obtuse. Mature: Elliptic/obtuse.
*Shape of apex*.—Lanceolate.
*Shape of base*.—Round.
*Texture*.—Shiny.
*Aspect*.—V-formed.
*Margin type*.—Serrate.
*Pubescence*.—None present.
*Color*.—Young leaves: Upper surface: Forest Green 22 8B 22. Lower surface: Forest Green 22 8B 22. Mature leaves: Upper surface: Dark Green 00 64 00. Lower surface: Dark Green 00 64 00.
*Petiole*.—Shape: Square. Length: 2 cm. Diameter: 0.5 cm. Color: 6B 8E 23.
*Veins*.—Type: Cross-venulate. Color: Upper surface: Olive 80 80 00. Lower surface: Olive 80 80 00.

FLOWER

Natural flowering season: May until October in Harderwijk, The Netherlands.
Blooming habit: Continuous from late spring through summer.
Bud (measurements made when cluster size was 3 cm.):
*Shape of cluster*.—Round.
*Diameter of cluster*.—3 cm.
*Number of buds per cluster*.—40-50.
*Shape*.—Ball.
*Length*.—0.3 cm.
*Width*.—0.3 cm.
Inflorescence:
*Shape*.—Round.
*Length*.—16-20 cm.
*Diameter*.—16-20 cm.
*Average number of flowers per inflorescence*.—40.
*Typical number of inflorescences per plant*.—6.
*Lastingness of an individual flower*.—8 weeks.
*Lastingness of an inflorescence*.—8 weeks.
Petaloids:
*Fertile flowers*.—Yes.
*Number per flower*.—5.
*Color*.—Upper surface: Pink FF C0 CB. Lower surface: Pink FF C0 CB.
*Shape*.—Lanceolate and attenuate.
*Length*.—0.3 cm.
*Width*.—0.3 cm.
*Apex*.—Triangular.
*Base*.—Flat.
*Margin*.—Erect.
*Texture*.—Shiny.
Petaloid sepals:
*Quantity*.—5.
*Shape*.—Pointed.
*Length*.—2 cm.
*Width*.—3 cm.
*Color*.—Upper surface: Multicolored; Hot Pink FF 69 B4, Pale Violet Red DB 70 93, and Olive 80 80 00. Lower surface: Multicolored; Hot Pink FF 69 B4 and Olive 80 80 00.
*Sterile flower sepal margin*.—Slightly serrate.
*Average size of sterile floret*.—2 cm.
*Sterile flower sepal color*.—When opening: AD FF 2F and F0 80 80. Fully opened: 22 8B 22 and F0 80 80. Fading: 22 8B 22 and F0 80 80.
Pedicels:
*Length*.—2 cm.
*Diameter*.—0.2 cm.
*Color*.—Multicolored; Hot Pink FF 69 B4 and Olive 80 80 00.
Peduncles:
*Length*.—3-4 cm.
*Diameter*.—0.3-0.4 cm.
*Texture*.—Smooth.
*Color*.—Olive 80 80 00.
Stamens (fertile flowers):
*Number per flower*.—10.
*Filament*.—Length: 0.3 cm. Color: FA EB D7.
*Anthers*.—Shape: Elongated oval. Length: 0.2 cm. Color: Medium Purple 93 70 DB.
*Pollen*.—Color: Beige F5 F5 DC. Amount: Abundant.
Pistils (fertile flowers):
*Number*.—3.
*Length*.—0.3 cm.
*Style*.—Length: 0.2 cm. Color: Light Pink FF B6 C1.
*Stigma*.—Shape: Long and oval. Color: FA EB D7. Size: 0.15 cm.
*Ovaries* (*superior*).—Length: 0.2 cm. Width: 0.2 cm. Color: Beige F5 F5 DC.
Fragrance: None observed.
Disease resistance: Tolerant to *Botrytis*.
Temperature tolerance: Very good as long as direct sunlight is limited; heat tolerance to 30° C. and frost tolerance to −15° C.
Drought tolerance: Medium.
Fruit: None observed.

I claim:

1. A new and distinct variety of *Hydrangea* plant substantially as shown and described herein.

* * * * *